United States Patent
Anderson et al.

(10) Patent No.: US 7,435,524 B2
(45) Date of Patent: Oct. 14, 2008

(54) PERMANENT, REMOVABLE TISSUE MARKINGS

(75) Inventors: Richard Rox Anderson, Lexington, MA (US); Susanna K. Mlynarczyk-Evans, San Francisco, CA (US); Craig A. Drill, New York, NY (US)

(73) Assignees: The General Hosptial Corporation, Boston, MA (US); Freedom-2, Inc., New York, NY (US)

( * ) Notice: Subject to any disclaimer, the term of this patent is extended or adjusted under 35 U.S.C. 154(b) by 0 days.

(21) Appl. No.: 11/876,410

(22) Filed: Oct. 22, 2007

(65) Prior Publication Data

US 2008/0044746 A1 Feb. 21, 2008

Related U.S. Application Data

(60) Continuation of application No. 11/651,190, filed on Jan. 8, 2007, now Pat. No. 7,285,364, which is a division of application No. 10/984,133, filed on Nov. 9, 2004, now Pat. No. 7,175,950, which is a division of application No. 10/340,407, filed on Jan. 10, 2003, now Pat. No. 6,814,760, which is a continuation of application No. 09/197,105, filed on Nov. 20, 1998, now abandoned.

(51) Int. Cl.
*G03F 7/004* (2006.01)
*G03F 7/039* (2006.01)

(52) U.S. Cl. .................. 430/138; 430/139; 430/944; 430/964; 106/31.03; 8/404; 428/404

(58) Field of Classification Search ............... 430/138, 430/139, 944, 964; 106/31.03; 8/404; 428/403
See application file for complete search history.

(56) References Cited

U.S. PATENT DOCUMENTS

| 2,487,557 A | 11/1949 | Jourgensen |
| 2,735,780 A | 2/1956 | Le Compte et al. |
| 3,011,899 A | 12/1961 | Bergman |

(Continued)

FOREIGN PATENT DOCUMENTS

DE 34 20 867 12/1985

(Continued)

OTHER PUBLICATIONS

Belfield et al., "Multiphoton-absorbing organic materials for microfabrication, emerging optical applications and non-destructive three-dimensional imaging," J. Phys. Org. Chem. 13:837-849 (2000).

(Continued)

*Primary Examiner*—Amanda C. Walke
(74) *Attorney, Agent, or Firm*—Fish & Richardson P.C.

(57) ABSTRACT

The present invention provides microparticles that create permanent tissue markings, such as tattoos, designed in advance for change and/or removal on demand, as well as methods for implanting the microparticles in tissue and changing and/or removing the resulting markings. Colored microparticles are constructed with specific electromagnetic absorption and/or structural properties that facilitate changing and/or removing tissue markings made using the microparticles by applying specific energy (such as electromagnetic radiation from a laser or flash-lamp) to the tissue marking site.

46 Claims, 3 Drawing Sheets

U.S. PATENT DOCUMENTS

| | | |
|---|---|---|
| 3,272,585 A | 9/1966 | Rafferty et al. |
| 3,640,889 A | 2/1972 | Stewart |
| 3,708,334 A | 1/1973 | Firth et al. |
| 3,873,687 A | 3/1975 | Demko |
| 4,155,886 A | 5/1979 | DeGoler |
| 4,214,490 A | 7/1980 | Chizek |
| 4,280,813 A | 7/1981 | DeGoler |
| 4,493,869 A | 1/1985 | Sweeney et al. |
| 4,610,806 A | 9/1986 | Rosen |
| 4,816,367 A | 3/1989 | Sakojiri et al. |
| 4,861,627 A | 8/1989 | Mathiowitz et al. |
| 4,891,043 A | 1/1990 | Zeimer et al. |
| 4,897,268 A | 1/1990 | Tice et al. |
| 4,898,734 A | 2/1990 | Mathiowitz et al. |
| 4,900,556 A | 2/1990 | Wheatley et al. |
| 4,921,757 A | 5/1990 | Wheatley et al. |
| 4,933,185 A | 6/1990 | Wheatley et al. |
| 4,937,119 A | 6/1990 | Nikles et al. |
| 5,041,292 A | 8/1991 | Feijen |
| 5,049,322 A | 9/1991 | Devissaguet et al. |
| 5,087,461 A | 2/1992 | Levine et al. |
| 5,157,412 A | 10/1992 | Kleinschmidt et al. |
| 5,217,455 A | 6/1993 | Tan |
| 5,234,711 A | 8/1993 | Kamen et al. |
| 5,330,565 A | 7/1994 | Saitoh et al. |
| 5,334,575 A | 8/1994 | Noonan et al. |
| 5,376,347 A | 12/1994 | Ipponmatsu et al. |
| 5,384,333 A | 1/1995 | Davis |
| 5,409,797 A | 4/1995 | Hosoi et al. |
| 5,445,611 A | 8/1995 | Eppstein et al. |
| 5,601,859 A | 2/1997 | Penaluna |
| 5,690,857 A | 11/1997 | Osterried et al. |
| 6,013,122 A | 1/2000 | Klitzman et al. |
| 6,060,072 A | 5/2000 | Konik et al. |
| 6,106,852 A | 8/2000 | Vineberg |
| 6,416,740 B1 | 7/2002 | Unger |
| 6,451,294 B1 | 9/2002 | Simon |
| 6,470,891 B2 | 10/2002 | Carroll |
| 6,663,852 B2 | 12/2003 | Simon |
| 6,800,122 B2 | 10/2004 | Anderson et al. |
| 6,814,760 B2 | 11/2004 | Anderson et al. |
| 6,881,249 B2 | 4/2005 | Anderson et al. |
| 2002/0074003 A1 | 6/2002 | Carroll |
| 2003/0159615 A1 | 8/2003 | Anderson et al. |

FOREIGN PATENT DOCUMENTS

| | | |
|---|---|---|
| FR | 2705615 | 12/1994 |
| JP | 137175 | 10/1980 |
| JP | 61047410 | 7/1986 |
| JP | 98202 | 4/1993 |
| WO | WO 93/04411 | 3/1993 |
| WO | WO 98/48716 | 11/1998 |
| WO | WO 2005/018741 | 3/2005 |

OTHER PUBLICATIONS

Taylor et al., "Light and Electron Microscopic Analysis of Tattoos Treated by Q-Switched Ruby Laser," The Journal of Investigative Dermatology, 97:131-136, (1991).

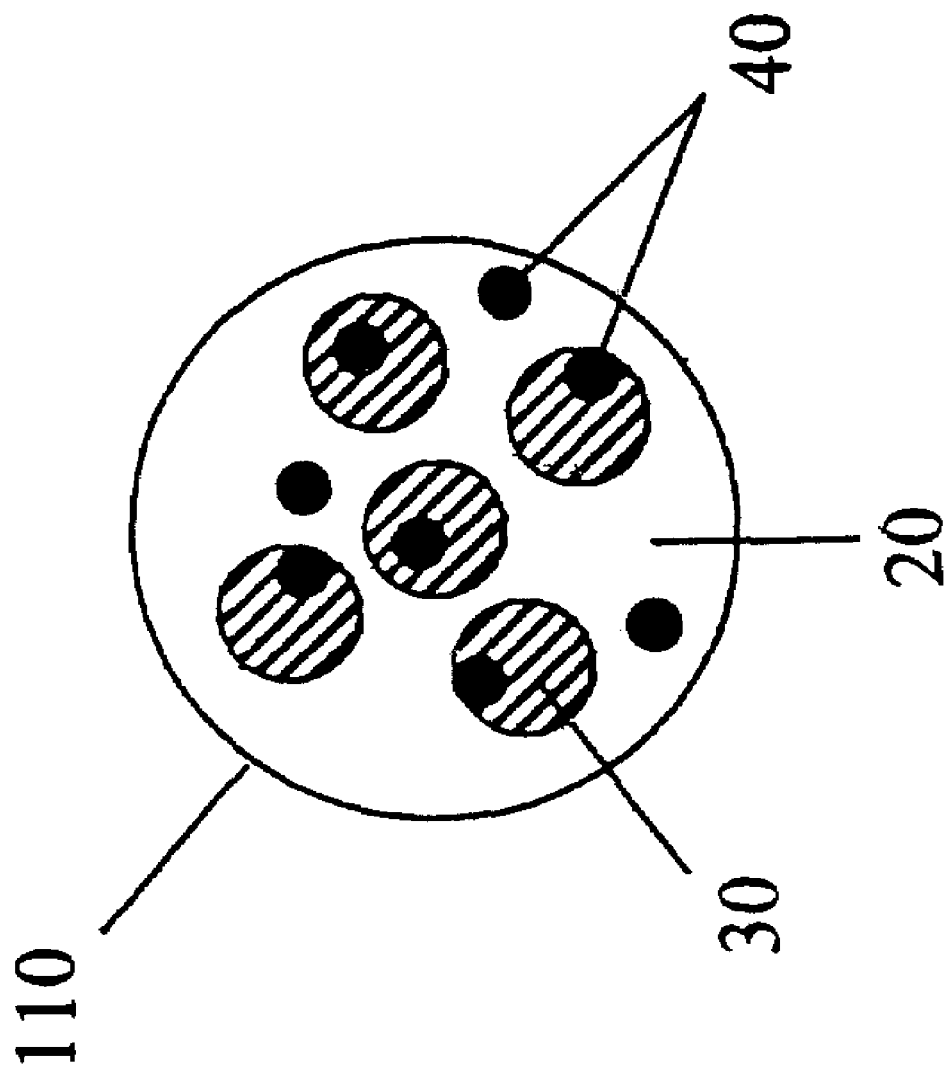

PERMANENT, REMOVABLE TISSUE MARKINGS

CROSS-REFERENCE TO RELATED APPLICATIONS

This application is a continuation application of and claims the benefit of U.S. Ser. No. 11/651,190, filed Jan. 8, 2007, now U.S. Pat. No. 7,285,364, which is a divisional application of U.S. Ser. No. 10/984,133, filed Nov. 9, 2004, now U.S. Pat. No. 7,175,950, which is a divisional application of U.S. Ser. No. 10/340,407, filed on Jan. 10, 2003, now U.S. Pat. No. 6,814,760, which is a continuation of U.S. Ser. No. 09/197,105, now abandoned, filed on Nov. 20, 1998, the contents of which are incorporated herein by reference in their entirety.

FIELD OF THE INVENTION

The invention relates to permanent tissue markings that can be changed or removed, or both, on demand.

BACKGROUND OF THE INVENTION

Tattoos have been used in almost every culture throughout history. They have been found on a five thousand year old human mummy, and decorated figurines suggest their use at least fifteen thousand years ago. Tattoos have been used for many purposes including identity, beauty, artistic and spiritual expression, medicine, and magic.

In the United States, statistics are not kept on tattooing but the practice has apparently been growing in popularity for the past few decades. The majority of tattoos are apparently obtained by people under forty years of age, including a significant proportion of teenagers. An estimated 2 million people are tattooed every year.

In the U.S. today, the uses of tattooing have expanded to include not only the familiar artistic tattoo, but also permanent makeup, for example, permanent eyebrows, eyeliner, lip liner, and lip color; corrective or reconstructive pigmentation, for example, repigmentation of scar tissue or areola reconstruction on mastectomy patients; medical markings, for example, marking gastrointestinal surgery sites for future monitoring; and identification markings on animals, for example, pedigree "tags" on purebred pets.

The tattooing procedure consists of piercing the skin with needles or similar instruments to introduce an ink that includes small particles of pigment suspended in a liquid carrier. During the healing process, some particles of pigment are sloughed from the skin surface and others are transported to the lymphatic system. What one sees as the tattoo are the remaining particles of pigment located in the dermis where they are engulfed by phagocytic skin cells (such as fibroblasts and macrophages) or are retained in the extracellular matrix.

To create a permanent tattoo one must implant pigments that are not dissolved or digested by living tissue. Primitive pigments probably consisted of graphite and other carbon substances. Modern pigments also include inorganic metal salts and brightly colored organometallic complexes.

Tattoo ink ingredients have never yet been regulated or fully disclosed to the public. Ink composition and pigment sources remain trade secrets. Allergic reactions to these unknown and/or undisclosed substances, rare but in some cases severe, have been reported at the time of tattooing, well after the time of tattooing, and after exposure to sunlight or laser treatments.

The long-term health effects, including potential toxicity and/or carcinogenicity of tattoo pigments, have not been studied and are not known. Unfortunately, these pigments, chosen for their permanence, are believed to remain in the body for life, concentrated in the lymph nodes, even if the visible tattoo is "removed" from the marked area, for example, by laser treatment.

A widely recognized problem with tattoos is that they cannot be easily removed. One survey indicated that about half of all Americans with tattoos at some point wish they could remove them. Dissatisfaction can stem from undesired social disapproval; from the appearance of a tattoo that may be poorly executed, out-of-style, or inaccurate (commonly in the case of name-containing vow tattoos); or from changes in the wearer's self-perception or lifestyle, which are especially likely for the increasing number of young customers.

Tattoo "removal" methods have included overtattooing without ink, dermabrasion, and surgical excision, all of which usually leave unacceptable appearance and/or scarring. The use of these removal methods was recorded as early as the first century A.D. in Rome, when soldiers returned from barbaric regions with tattoos that were unacceptable to society.

In fact, there had been no significant technological advances in tattoo removal methods until the 1960s when Dr. Leon Goldman pioneered the use of pulsed lasers. This method was improved in the 1980s by Dr. R. Rox Anderson, and has since become widely practiced. Removal can now also be achieved using variable-wavelength intense pulsed light sources (flash-lamps).

Ideally, short, powerful light pulses are absorbed specifically by tattoo pigment particles with little or no absorption by surrounding tissue, thereby causing the particles of pigment to break apart with minimal damage to neighboring skin structures. Skin injury is extremely local and scarring is uncommon. Instantaneously, some particles of pigment are apparently broken into pieces which have far less optical absorption than the original particles, and thus are less visible. During the healing process, many particles are physically removed from the tattoo site while others remain in the dermis as a residual tattoo.

Despite advantages over older methods, laser or flash-lamp removal of standard tattoos is not ideal. A treatment course requires an average of approximately eight laser treatments at a cost of several hundred dollars apiece. The treatments must be spaced at least one month apart and can be painful. Because a laser must be chosen for absorption of its emission wavelength by the particular pigment, multiple lasers are needed to treat multicolored tattoos effectively; however, a removal practitioner's office may not offer the optimal laser(s) to treat a specific tattoo. Certain pigments, including many greens, remain difficult to remove, and there is currently no commercially available tattoo removal laser which effectively treats most yellow pigments. Intense visible light sometimes targets the skin's natural epidermal pigment, melanin, resulting in temporary or permanent hypo- or hyperpigmentation, especially in dark or tanned skin, and/or hair loss in the area. In addition, some tattoo pigments undergo color changes in response to treatment. For example, inks used for permanent makeup often contain certain iron, titanium, or other oxides which are irreversibly blackened upon exposure to Q-switched lasers, and cannot always be removed by further treatments.

After the treatment course, most patients can expect that a tattoo will not be prominently visible or recognizable, but it is unusual to be able to restore the skin to its original pre-tattoo appearance. Because of the numerous drawbacks, only a fraction of those people who are unhappy with their tattoos pursue tattoo removal.

SUMMARY OF THE INVENTION

The invention provides for permanent markings (such as tattoos) in tissue (typically living tissue, such as skin) that are designed in advance to be easily changed and/or removed on demand. These markings are created using indispersible microparticles that consist of or contain chromophores. These microparticles are designed in advance with one or more specific properties (such as electromagnetic and/or structural properties) that allow the microparticles to be altered by exposure to a specific energy (such as a specific electromagnetic radiation) to change and/or remove the tissue markings.

In general, the invention features a method of applying to a tissue a detectable marking that can be changed or removed, or both, on demand, by obtaining colored microparticles each including a chromophore and having a specific property that is designed in advance to enable the microparticles to be altered when exposed to a specific energy (for example, electromagnetic radiation such as near-infrared (near-IR), infrared (IR), near-ultra violet (near-UV), or high intensity visible radiation); and implanting into the tissue a sufficient number of the colored microparticles to form a detectable tissue marking, wherein the tissue marking is permanent until the specific energy is applied to alter the microparticles to change or remove, or both, the detectable marking. In this method, the chromophore or an additional material can provide the specific property, which can be, for example, the absorption of the specific energy, photochemical reactivity, or thermochemical reactivity when the microparticles are exposed to the specific energy. The specific energy can be applied only once to change or remove, or both, the detectable marking.

In certain embodiments, the colored microparticles each include (i) an indispersible, biologically inert coating, (ii) a core enveloped within the coating, wherein the core includes the chromophore which is detectable through the coating and is dispersible in the tissue upon release from the microparticle, and, optionally (iii) an absorption component that absorbs the specific energy and that is located in the coating or the core, or both; and the specific property is the absorption of the specific energy to rupture the microparticle, releasing the chromophore which disperses in the tissue, thereby changing or removing, or both, the detectable marking, wherein the coating, the core, or the optional absorption component, or any combination thereof, provide the specific property.

For example, the dispersible chromophore can be dissolved or metabolized when released into the tissue, or the chromophore can be insoluble and have a size and configuration such that it is physically relocated from the detectable marking by biological processes when released into the tissue. The chromophore can be or include rifampin, β-carotene, tetracycline, indocyanine green, Evan's blue, methylene blue, FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), or FD&C Yellow No. 6 (Sunset Yellow FCF). The chromophore can be any colored substance approved by the United States Food and Drug Administration for use in humans. In certain embodiments, the chromophore can be detected by the naked eye under normal lighting conditions or when exposed to UV, near-UV, IR, or near-IR radiation.

In other embodiments, the coating, the chromophore, or the optional absorption component, or any combination thereof, absorb specific electromagnetic radiation. The coating can be made of or include a metal oxide, silica, glass, fluorocarbon resin, organic polymer, wax, or a combination thereof. The coating can be substantially visibly transparent and absorb near-IR radiation, for example, at a wavelength between about 750 nm and about 2000 nm. The absorption component can be or include Schott filter glass, graphite, carbon, a metal oxide, an acrylate polymer, or a urethane polymer. The coating can itself absorb, or include an absorption component that absorbs, near-IR, IR, near-UV, or high intensity visible radiation.

In another embodiment, the coating can include pores of a size sufficient to allow the dispersible chromophore to leach out of the microparticle, for example, over a period of weeks or months, so that the tissue marking disappears at a given time. This provides tissue markings that fade slowly after microparticle implantation. These markings can also be removed at once upon exposure to the specific energy. The microparticles can also include multiple cores enveloped within one coating.

The invention also features a method in which the colored microparticles each include (i) an indispersible, biologically inert coating, (ii) a core enveloped within the coating, wherein the core includes the chromophore which is detectable through the coating and is altered upon exposure of the microparticle to the specific energy (such as near-infrared or infrared radiation), and optionally (iii) an absorption component that absorbs the specific energy and that is located in the coating or the core, or both; and in which the specific property is the ability of the chromophore to be altered upon exposure of the microparticle to the specific energy, thereby changing or removing, or both, the detectable marking, wherein the coating, the core, or the optional absorption component, or any combination thereof, provide the specific property. In this embodiment, the chromophores need not be dispersible, and the microparticles are not necessarily ruptured.

For example, the chromophore can be altered by losing its color or by changing from an initial color to a different color upon exposure to the specific energy. The microparticle can further include a sub-microparticle that includes a bleaching agent that is released from the sub-microparticle upon exposure of the microparticle to the specific energy, thereby bleaching the chromophore (for example, rendering it substantially invisible). The bleaching agent can be a peroxide, hypochlorite, excited oxygen species, or free radical. The chromophore can be pH-sensitive, and the bleaching agent is an acid, a base, or a buffer capable of effecting a pH transition within the core that bleaches the chromophore.

The photobleachable chromophore can be Rose Bengal, rhodamine compounds, coumarin compounds, dye-paired ion compounds, cationic dye-borate anion complexes, or bis (diiminosuccino-nitrilo)metal complexes. The chromophore can also be thermolabile, and exposure of the microparticle to the specific energy heats and alters the chromophore. In this method, the absorption component can be Schott filter glass, graphite, carbon, a metal oxide, an acrylate polymer, or a urethane polymer.

The methods can be used to mark a variety of tissues including skin, iris, sclera, dentin, fingernails, toenails, tissue beneath fingernails, tissue beneath toenails, tissue inside the mouth, and tissue lining internal body passages. In these methods, the specific energy can be applied at a wavelength, at an intensity, or for a duration, or any combination thereof, insufficient to completely remove or change the detectable marking, thereby partially removing or changing, or both, the detectable marking. The specific energy can be applied only once to effect the rupture or alteration.

In another aspect, the invention features a method of changing or removing, or both, a detectable marking created by implanting into tissue a sufficient number of colored microparticles each comprising a chromophore and having a specific property that is designed in advance to enable the microparticles to be altered when exposed to a specific energy, by exposing the detectable marking to the specific energy for a time sufficient to alter the microparticles, thereby changing or removing, or both, the detectable tissue marking. In this method, the microparticles are altered to become substantially undetectable, thereby removing the tissue marking, for example, by rupturing and releasing the chromophore, or by losing the color of the chromophore. Alternatively, the microparticles can be altered by changing from an initial color to a different color, thereby changing the color of the tissue marking. In this method, the colored microparticles can be those described herein.

In yet another aspect, the invention features colored microparticles that includes (i) an indispersible, biologically inert coating that provides from about 10 to about 95 percent of the volume (such as 15 to 25 or 35 percent) of the microparticle (and that renders the chromophores less dispersible or indispersible), (ii) a core enveloped within the coating, wherein the core is or includes a chromophore that is detectable through the coating and is dispersible in living tissue upon release from the microparticle, and, optionally (iii) an absorption component that absorbs a specific energy (such as near-infrared or infrared radiation) and that is located in the coating or the core, or both; wherein the coating, the core, or the optional absorption component, or any combination thereof, is designed in advance to absorb the specific energy to rupture the microparticle, releasing the chromophore which disperses in the living tissue.

In another aspect the invention features a colored microparticle that includes (i) an indispersible, biologically inert coating comprising from about 10 to about 95 percent of the volume of the microparticle (such as 40 or 50 to 80 or 90 percent), (ii) a core enveloped within the coating, wherein the core is or includes a chromophore that is detectable through the coating and is altered upon exposure of the microparticle to a specific energy (such as near-infrared, infrared, ultraviolet, or high-intensity visible radiation), and optionally (iii) an absorption component that absorbs the specific energy and that is located in the coating or the core, or both; wherein the coating, the core, or the optional absorption component, or any combination thereof, is designed in advance to absorb the specific energy to alter the chromophore.

These microparticles can have a radius of from 50 nanometers to 100 microns. The coating can be or include a metal oxide, silica, glass, fluorocarbon resin, organic polymer, wax, or any combination thereof. In certain embodiments of the rupturable microparticles, the absorption component forms a plug sealing a hole in the coating, wherein the plug is destroyed upon exposure to the specific energy to open the hole in the coating. Alternatively, the coating can include one or more absorption components that when exposed to the specific energy cause the coating to break open. The colored microparticles can be sterilized.

The colored microparticles (preferably the microparticles with a non-rupturing outer coating) can further include a sub-microparticle (that can have its own coating), for example, in the core, that includes a bleaching agent (such as a peroxide, hypochlorite, excited oxygen species, or free radical) that is released from the sub-microparticle upon exposure of the microparticle to the specific energy, thereby bleaching the chromophore. The chromophore can be photobleachable, and exposure of the microparticle to the specific energy renders the chromophore substantially invisible. The chromophore can be thermolabile, and exposure of the microparticle to the specific energy renders the chromophore substantially undetectable or invisible.

The invention also features tissue marking inks that include the colored microparticles and a liquid carrier, which can include alcohol, water, or glycerin, or any combination thereof.

Additional embodiments are possible wherein the microparticles do not necessarily include a coating or encapsulation, and the microparticles are designed in advance with strong absorption of specific energy which renders the chromophores (1) dispersible from the microparticles or (2) invisible.

A significant feature of composite microparticles, especially such as those that are ruptured, is that a common property (such as a specific electromagnetic absorption peak) can be included in diverse microparticles (having multiple colors). These diverse microparticles can include a common material (in composite constructions) or materials with similar absorption spectra. For example, this design allows removal of multiple colors in a tissue marking through common treatment with a specific type of energy (such as one wavelength emitted by one existing laser).

As used herein, a "microparticle" is a particle of a relatively small size, not necessarily in the micron size range; the term is used in reference to particles of sizes that can be implanted to form tissue markings and thus can be less than 50 nm to 100 microns or greater. In contrast, a "nanoparticle" is specifically a particle in the nanometer ($10^{-9}$) size range, for example, 15 nm or 500 nm. A micro- or nanoparticle may be of composite construction and is not necessarily a pure substance; it may be spherical or any other shape.

As used herein, a "dispersible" substance (such as a chromophore) is (1) dissolved by (and is soluble in) bodily fluids, for example, those within a cell or tissue; (2) metabolized (including digested) by living tissue and/or cells into one or more new chemical products; and/or (3) of a size (on average no larger than about 50 nanometers, but in some cases necessarily much smaller, for example, less than about 5 nm), made of a material, and configured such that normal bodily processes result in its physical relocation from tissue (from cells or from extracellular matrix).

As used herein, an "indispersible" substance (such as a coating material or an individual microparticle) does not disintegrate, dissolve, or become metabolized in tissue. "Indispersible" microparticles are also large enough on average (generally greater than about 50 nm, but depending on the material as small as 5 nm or even smaller) and have a configuration on average such that when a plurality is implanted into tissue a sufficient number is retained to form a detectable marking, even though some number of the individual microparticles may be relocated from the tissue marking site through biological processes (such as lymphatic transport).

An "inert" or "biologically inert" substance (such as the coating material of a microparticle) generally creates no significant biochemical, allergic, or immune response after the normal healing period when implanted into living tissue.

A "chromophore" is broadly defined herein as a substance (solid, liquid, or gas) that has color or imparts a color to the intact microparticles (including when the substance itself lacks color, for example, a clear gas, but scatters electromagnetic waves, for example, light, and thus may appear colored, for example, white, blue, green, or yellow, depending on its scattering properties) under some conditions, for example, all of the time or after exposure to a certain wavelength (such as in a fluorescent substance). For example, a chromophore can be a fluorescent, phosphorescent, wavelength up-converting, or other substance that may normally be substantially invisible, but that emits ultraviolet, visible, or infrared wavelengths during and/or after exposure to wavelengths from a particular region of the electromagnetic spectrum. A chromophore can also be a substance that reversibly or irreversibly changes color spontaneously or in response to any stimulus.

"Color" is broadly defined herein as a detectable (that is, visible or able to be made visible under certain lighting conditions, or able to be detected using a device, for example, an infrared camera) property determined by a substance's electromagnetic absorption and/or emission spectrum (that is, in the ultraviolet, near-ultraviolet, visible, near-infrared, infrared, and other ranges). Black and white are colors under this definition.

As used herein, a substance (such as a chromophore) is "invisible" when essentially no color can be detected (such as in a tissue marking site) apart from the normal coloration of the substance's surroundings (such as skin or other tissue) by the naked eye under normal lighting conditions, for example, diffuse sunlight or standard artificial lighting. A substance is "undetectable" when it is invisible to the naked eye under normal lighting conditions, and also invisible by the naked eye, or a device, under any other lighting conditions (such as fluorescent, UV, or near-infrared).

As used herein, a "permanent tissue marking" or "tissue marking" is any mark created by the introduction of microparticles of the invention into tissue, typically living tissue, with the intention of permanent or long-term endurance. Markings can be any color and must be detectable, for example, by the naked eye or by an infrared detection device, when exposed to electromagnetic radiation in one or more regions of the spectrum, for example, the visible or near-infrared regions. A permanent marking is generally a marking that remains visible or otherwise detectable until it is exposed to a specific energy. However, in certain embodiments, a permanent marking can be a mark that is designed in advance to disappear after a predetermined time, for example after one or several months, and/or can be removed by exposure to a specific energy before the predetermined time.

As used herein, a "tattoo" is a type of tissue marking wherein the tissue is usually skin. "Standard tattoos" and the pigments used to create them have not been designed in advance for change and/or removal.

As used herein, a "non-invasive" procedure for creating a tissue marking implants microparticles into the tissue without the use of an implement that enters the surface of the tissue. Forces that can be applied to microparticles to achieve non-invasive tattooing include ballistic, electrical (such as through iontophoresis or electroporation), magnetic, electromagnetic, ultrasonic, chemical, and chemical gradient forces, or any combination of these forces.

As used herein, "removal" of a tissue marking means either the physical removal of the substance(s) that create the appearance of the marking, or the destruction or facilitated loss of some chromophoric property that renders the marking invisible. Thus, all, some, or none of the components (chromophores, coating material, etc.) of the microparticles may be physically relocated from the tissue when a tissue marking is "removed."

Tissue marking microparticles that are "designed in advance" for change and/or removal means that the materials and/or structure of the microparticles are selected and/or engineered, and intended, to facilitate change and/or removal of the tissue marking. It in no way implies that a pre-determined removal method must be used, that this or another removal method is the best method, or that a removal method is explicitly outlined at the time of microparticle design. Multiple removal methods may be acceptable for removing a given marking. Adjustments made to any proposed method may affect removal efficacy positively, negatively, or not at all.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

The invention provides several advantages over standard tattoos and their removal. Standard tattoos are made using unregulated pigments of undisclosed nature which, once implanted, are in direct contact with living tissue for the recipient's life, even if no longer visible at the tissue marking site. A course of many treatments to remove a standard tattoo is not always successful, yet it is time-consuming and expensive, may expose the tissue to a damaging amount of radiation, requires guesswork and experimentation on the part of the practitioner, and, in the case of multicolored tattoos, may require multiple lasers.

Through practice of the methods disclosed herein, tissue marking removal treatments can become essentially 100% effective. The associated costs of removal in terms of time (such as length of treatment course) and/or money can be reduced compared to standard tattoo removal treatment.

By using tissue markings specifically designed in advance for removal, the invention can reduce the total dose of energy (such as laser radiation) to which the tissue marking site must be exposed for removal. The incidence of patient pain and complications including skin injury can be reduced compared to treatments to remove standard tattoos, which can include more irradiation sessions at higher fluences.

In addition, the parameters (such as fluence and pulse duration) for removal of tissue markings of the invention can be optimized in controlled studies. When provided to practitioners, guesswork and experimentation can be eliminated from treatments to remove tissue markings of the invention and treatment outcome will be predictable.

Whereas removal of standard multicolored tattoos requires treatment with multiple laser wavelengths absorbed by different pigments, microparticles of the invention can be constructed such that one type of energy (such as one wavelength) can target diverse microparticles. One benefit of this feature, if multicolored microparticles are designed in advance for removal by a single wavelength, is that removal practitioners will need only one device to treat all patients for removal of tissue markings of the invention. Currently, practitioners do not always have all of the lasers needed for optimal treatment of standard multicolored tattoos, in part because tattoo removal devices are expensive (approximately $30,000 for a 3 Joule, Q-switched ruby laser to about $100,000 for a flash-lamp).

In addition, the invention can reduce short- and long-term health risks associated with standard tattoo pigments. Microparticles of the invention can be designed to be inert and non-toxic when implanted in tissue and/or can be constructed using materials that are already accepted for long-term use in the human body.

According to important embodiments of the invention, chromophores are encapsulated in inert materials to provide the microparticles for tissue marking. These chromophores have minimal direct contact with the recipient's body; whereas, in standard tattoos, the chromophoric pigments are directly in contact with the body in tissue cells and are thought to be stored in the lymph nodes for life.

Furthermore, the composition of tissue marking inks made with the new microparticles will be known and can be disclosed in advance to allow those with recognized allergies to avoid implantation and to provide critical information for treating reactions.

Other features and advantages of the invention are apparent from the following detailed description and from the claims.

BRIEF DESCRIPTION OF THE DRAWINGS

FIG. 5 is a schematic cross-sectional view of another embodiment of a colored microparticle.

DETAILED DESCRIPTION

Microparticles capable of providing selectively removable tissue markings must meet several criteria. First, they must be or contain a chromophore that is detectable and has a color that is different from the color of the tissue. Second, the microparticles and/or their chromophoric properties must be removed by a specific externally applied treatment. Third, the microparticles must be indispersible, as described herein, in the tissue under normal physiological conditions. Fourth, any component of the microparticles which will at any time (such as during implantation or removal or while the marking exists) come into contact with the tissue must be substantially biologically inert, unreactive, or safely metabolized.

It is theoretically possible to select a palette of pure materials that meet all four criteria for use as tissue marking microparticles. A more efficient way to design the microparticles is to prepare them as composites of two or more materials. The combination of several materials' properties can more easily satisfy the four criteria. For example, the chromophore may satisfy criteria 1, 2, and 4, and a coating may satisfy criteria 3 and 4.

Microparticles

Microparticles of the invention are generally composed of a biologically inert coating material enveloping at least one core comprising one or more chromophores. The microparticles have a diameter of about 50 nm to about 100 microns, but may be smaller or larger as long as the microparticles can be implanted into a tissue to provide a tissue marking. They can be spherical, as shown in the figures, or any other shape.

Figure 2:
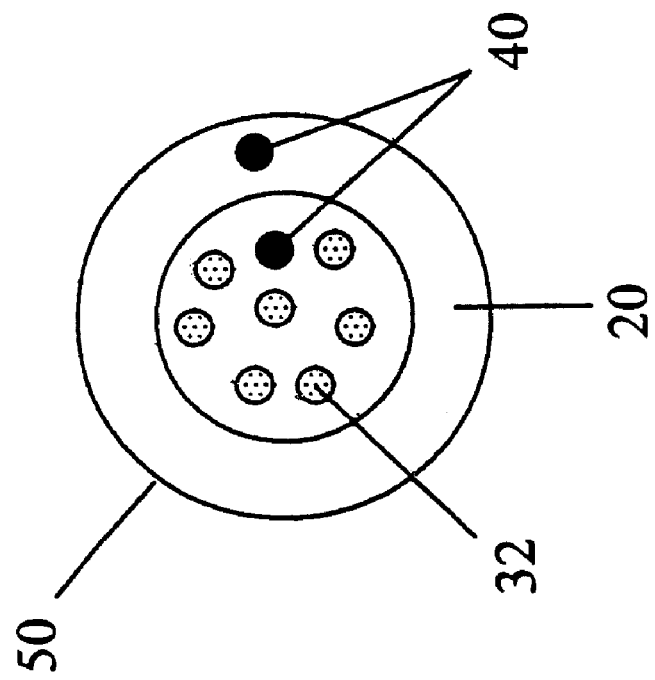
FIG. 2 is a schematic cross-sectional view of a colored microparticle containing chromophore nanoparticles.
Figure 1:
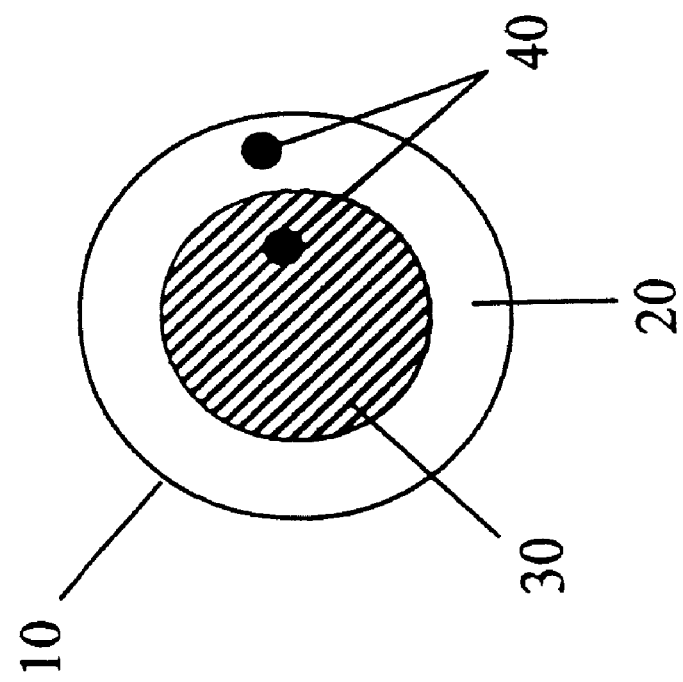
FIG. 1 is a schematic cross-sectional view of a colored microparticle.

FIG. 1 shows a basic microparticle 10, which includes a coating 20 encapsulating a core containing chromophore(s) 30. As shown in microparticle 50 of FIG. 2, the core may contain discrete chromophore nanoparticles 32.

Figure 3:
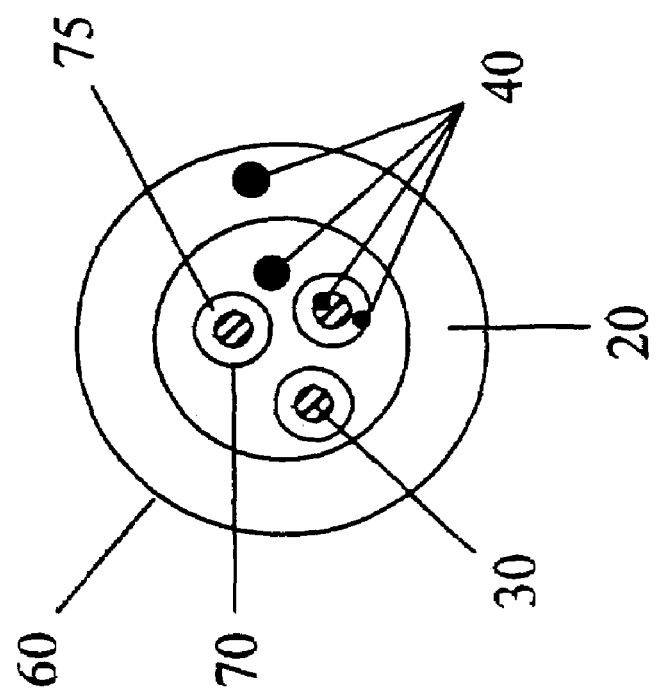
FIG. 3 is a schematic cross-sectional view of a colored microparticle containing sub-microparticles comprising encapsulated chromophores.

In certain cases, as depicted in FIG. 3, it may be useful to encapsulate a plurality of composite sub-microparticles 70, comprising chromophore(s) 30 and substantially transparent coating 75 (which may or may not be the same material as used in coating 20), in coating 20 to form microparticle 60. Sub-microparticles 70 can be any size as long as they fit within the microparticle 60.

Figure 4:
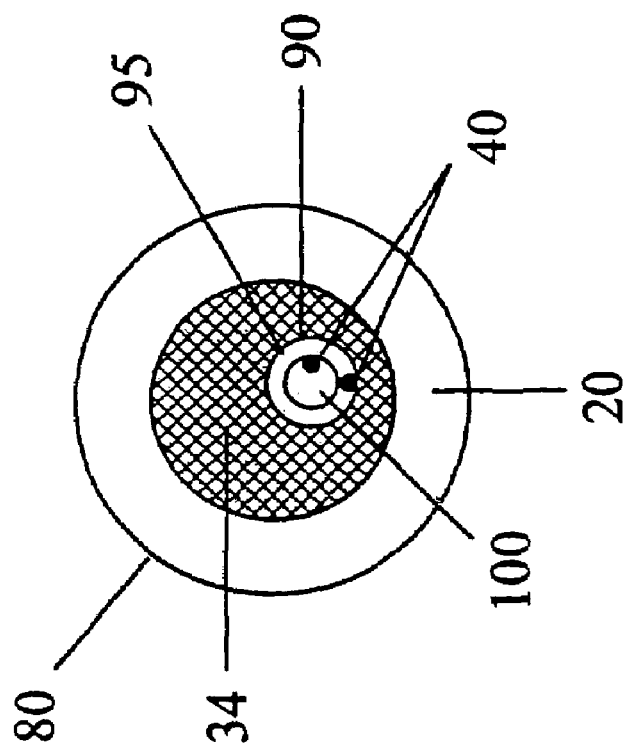
FIG. 4 is a schematic cross-sectional view of a colored microparticle containing a bleachable chromophore and a sub-microparticle comprising an encapsulated bleaching agent.

In another embodiment, illustrated schematically in FIG. 4, bleachable chromophore(s) 34 and composite sub-microparticle(s) 90 (comprising bleaching agent(s) 100 and coating 95) are encapsulated in coating 20 to form microparticle 80.

FIG. 5 depicts an optional configuration for the microparticle in FIG. 1, where two or more cores containing chromophore(s) 30 can be present within the coating 20 of a single microparticle 110. Analogous multi-core versions of the microparticles in FIGS. 2 to 4 can also be constructed.

Generally, coating 20 and/or 75 or 95 is made from any substantially transparent material(s) (that is, a material that allows the encapsulated chromophore to be detected, for example, seen) that is indispersible (and is therefore generally retained in tissue) and is biologically inert under physiological conditions. The coating can have a thickness ranging from about 0.05 r (about 86% core loading, 14% coating, by volume) to about 0.6 r (about 6.4% core loading, 93.6% coating, by volume), where r is the microparticle radius. The coating can be from about 10 to about 95 percent of the total volume of a microparticle.

Any substance or combination of substances that imparts color to a microparticle and which is usually, but not necessarily in all cases, inert and unreactive in the body, may be chosen as chromophore(s) 30, 32, or 34, as long as it is subject to removal (or alteration) according to one of the two general methods described in detail hereafter, or another suitable method.

Depending on the planned removal method of the microparticles depicted in FIGS. 1 to 5, an additional absorption component(s) 40 may or may not be incorporated into coatings 20, 75, or 95, and/or mixed with chromophore(s) 30, chromophoric nanoparticles 32, or bleaching agent(s) 100.

The microparticles schematically depicted herein and described generally above can be constructed in two embodiments according to the intended removal method (except for microparticle 80 which is specific to a single removal method). In the first embodiment, microparticles can be constructed to contain dispersible chromophores that are removed when microparticles are made permeable, for example, by rupture of a coating. In the second embodiment, microparticles can contain chromophores that are rendered invisible without rupturing the microparticles.

More specifically, according to the first embodiment, microparticles 10, 50, 60, and 110 can contain dispersible chromophore(s) 30 or 32. Tissue markings made using these microparticles can be removed when desired using a method wherein the tissue marking is exposed to specific electromagnetic radiation which ruptures the microparticles. For example, the microparticles can rupture as the result of heating, for example, when the coating 20 and/or 75, chromophore(s) 30 or 32, or additional absorption component(s) 40 absorb the specific radiation. In this embodiment, when the chromophores are dispersed from the tissue marking site, the tissue marking disappears; this can occur over the course of several minutes to several weeks following irradiation.

Microparticles 10, 50, and 110 which contain dispersible chromophores(s) 30 and 32 can also be constructed with porous coatings such that the chromophore(s) leaches out and is dispersed over time; if desired, these microparticles can also be designed in advance for removal using specific electromagnetic radiation as in the above description.

According to the second embodiment, microparticles 10, 50, 60, 80, and 110 can contain specific encapsulated chromophores 30, 32, or 34 whose chromophoric properties can be changed to become invisible when the microparticle is exposed to a specific type of electromagnetic radiation, for example, pulses from a laser operating at a specific wavelength. In microparticles 10, 50, 60, or 110, this radiation must cause chromophore(s) 30 or 32 to be photobleached, oxidized, reduced, thermally altered, or otherwise destroyed, usually through absorption of the radiation by the chromophore(s); additional absorption component 40 is usually absent from the coating material in this embodiment.

In microparticle 80, this radiation must cause bleaching agent 100 to come into contact with bleachable chromophore(s) 30, usually through rupture of sub-microparticle(s) 90 via absorption of radiation by coating 95, bleaching agent 100, or additional absorption component(s) 40.

The chromophoric properties of a tissue marking made using these microparticles 10, 50, 60, 80, and 110 can be removed when desired using a method wherein the tissue marking is exposed to the specific electromagnetic radiation described above. In this embodiment, microparticles are not necessarily ruptured, and the chromophores are not necessarily released into the bodily fluids, but the microparticles become invisible. Thus, the tissue marking is removed during or after irradiation, usually within milliseconds to minutes, although none of the components of the microparticles are necessarily physically relocated from the tissue.

Certain aspects of the design of the several microparticles described herein may be interchanged or omitted, yielding useful microparticles. These and other types of microparticles are within the scope of the invention and will be useful if they are in the size range capable of providing tissue markings and if they satisfy the four criteria set forth at the beginning of this Detailed Description.

Coating Materials

The material(s) for coating 20 must be both indispersible and biologically inert and is preferably substantially visibly transparent. Substances fitting these criteria which are capable of encapsulating chromophores useful in the invention include waxes with a melting point substantially above body temperature, for example, natural waxes, synthetic waxes, and mixtures, specifically POLYWAX™ and carnauba wax; plastics and organic polymers, for example, parylenes, polyamide, polyvinyl acetate, urea formaldehyde, melamine formaldehyde, ethylene acrylate, cyanoacrylates, butadiene-styrene, and specifically biocompatible materials such as EPO-TEK™ 301 and 301-2, manufactured by Epoxy Technology, Billerica, Mass.; metal oxides, for example, $TiO_2$, silica ($SiO_2$), BIOGLASS™, KG-3 and BG-7 manufactured by Schott, Inc., Germany, and other glasses ($SiO_2$ plus any one or more of the following: $Na_2O$, $CuO$, $B_2O_3$, $MgO$, $Al_2O_3$, $P_2O_5$, and others); inorganic fluorine-containing compounds such as $MgF_2$; and fluorocarbons such as TEFLON™.

In some embodiments, coating 20 is made of a material or includes specific absorption component(s) 40 that strongly absorbs in a particular spectral region, for example, ultraviolet, visible, infrared (such as part of the near-infrared from 800 to 1800 nm), microwave, or radio wave. The choice of such a material allows microparticles to be selectively heated and ruptured by radiation (such as from a laser) near the absorption maximum of said material, thereby releasing dispersible chromophores. For reasons of avoiding electromagnetic radiation absorption by surrounding tissue during removal treatment, the spectral region from about 800 nm to 1800 nm is most desirable, as described in more detail in the Removal Methods section.

The entire coating 20 can be made of an absorbing material allowing rupture through absorption of specific electromagnetic radiation, for example, by differential heating which fractures the coating, or indirect heating of the central core and rapid expansion which explodes the coating.

Other useful variations of this embodiment include making a small portion of coating 20 with an absorbing material, or adding specific absorption component(s) 40. Irradiation then selectively affects the absorbing portion of the coating, causing the microparticle to rupture and its contents to be exposed to bodily fluids. The absorption component 40 can act like an "egg tooth" that ruptures the coating or like a "plug" that is destroyed to allow the chromophore to escape from the coating.

Examples of useful materials for constructing infrared-absorbing coatings 20 or specific absorption component(s) 40 are Schott filter glasses that absorb certain near-infrared wavelengths and are transparent or nearly transparent in visible light at the thicknesses of the coatings used in the microparticles. For example, KG-3 filter glass (Schott, Inc.) is designed to absorb infrared light at 1000 to 1400 nm, with a maximum at 1200 nm. BG-7 filter glass (Schott, Inc.) is designed to have an absorption maximum at 800 nm. Other examples of useful infrared- or near-infrared-absorbing materials include graphite and other forms of carbon; metals, metal oxides, and metal salts; and polymers such as acrylate and urethane.

Useful materials for absorption component(s) 40 which absorb in non-infrared regions of the electromagnetic spectrum include ferrites (such as iron oxides) which strongly absorb short, high intensity pulses of microwaves or radio waves. Use of these materials allows the microparticles to be heated and ruptured when irradiated with microwaves or radio waves of the proper wavelength, intensity, and pulse duration.

Electromagnetic absorbing materials that have a color under visible light can also be used for the coating material if that color is desired, or is eliminated, for example, photobleached, by exposing the material to a specific type of radiation. If used as absorption component(s) 40 (and in some cases even as coating 20), these materials may be effectively invisible because of the small amounts/thicknesses in the microparticles.

In some instances, it may be desirable to provide a coating 20 for microparticle 10 that is porous. For example, a porous coating enables chromophores to leach slowly out of microparticles to provide a tissue marking that lasts for a specific length of time, for example, a few weeks or months. Tissue markings made from such porous microparticles fade over time until the chromophores have leached out of the microparticles. The length of time required for the marking to become invisible can be controlled by adjusting the size and number of the pores in coating 20. Pores can be introduced into coatings during the encapsulation procedure.

Chromophores

Chromophore(s) 30, 32, or 34 can be made from any appropriate solid, liquid, or gaseous material that has chromophoric properties. In general, useful chromophores include stains, dyes, colored drugs and proteins, and other materials. Preferably, chromophores are biologically inert and/or non-toxic (ideally they are non-carcinogenic, non-allergenic, and non-immunogenic) such as those approved by the FDA for use within the body. However, they need not necessarily be known to be non-toxic in those embodiments in which the coating is impervious to bodily fluids and is maintained intact, with internal chromophores altered to become invisible, because the material remains encapsulated within an impermeable, inert coating.

Chromophores may be mixed in combinations before or after encapsulation, so that it may only be necessary to select a small number of different chromophores to obtain a broad range of colors for various tissue marking purposes. For example, the pure chromophores can be encapsulated separately and afterwards different colors may be mixed to form intermediate colors and shades (yellow microparticles may be mixed with blue microparticles to form a green mixture). Combinations of two or more unreactive chromophores can be mixed to form desired colors and shades, and then encapsulated to form microparticles. Optionally, as illustrated schematically in FIG. 3, pure chromophores 30 may be separately encapsulated to form sub-microparticles 70, and then different colored sub-microparticles can be mixed together (or with unencapsulated chromophores) to form desired colors and shades. The mixture can then be encapsulated in coating 20 to form a microparticle having a perceived color resulting from the blend of the differently colored chromophores.

Useful dispersible chromophores include: drugs and dyes such as rifampin (red), β-carotene (orange), tetracycline (yellow), indocyanine green (such as Cardio-Green™), Evan's blue, methylene blue; soluble inorganic salts such as copper sulfate (green or blue), $Cu(NH_3)^{2+}$ (dark blue), $MnO_4$ (purple), $NiCl_2$ (green), $CrO_4$ (yellow), $Cr_2O_7^{2-}$ (orange); proteins such as rhodopsin (purple and yellow forms) and green fluorescent protein (fluoresces green under blue light); and any of the Food and Drug Administration (FDA) approved dyes used commonly in foods, pharmaceutical preparations, medical devices, or cosmetics, such as the well-characterized non-toxic sodium salts FD&C Blue No. 1 (Brilliant Blue FCF), FD&C Green No. 3 (Fast Green FCF), FD&C Red No. 3 (Erythrosine), FD&C Red No. 40 (ALLURA™ Red AC), FD&C Yellow No. 5 (Tartrazine), and FD&C Yellow No. 6 (Sunset Yellow FCF). Of these FD&C dyes, Yellow No. 5 is known to produce occasional allergic reactions.

Additional FDA approved dyes and colored drugs are described in the *Code of Federal Regulations* (CFR) for Food and Drugs (see Title 21 of CFR chapter 1, parts 1-99). The table below lists a number of suitable chromophores, their Chemical Abstract Service (CAS) Registration Numbers, colors, and absorption maxima.

TABLE

| Chromophore | CAS Reg. No. | Color | Abs. Max. |
|---|---|---|---|
| Yellow No. 5 | 1934-21-0 | yellow | 428 |
| b-carotene | 7235-40-7 | orange | 466 |
| rifampin | 3292-46-1 | red | 475 |
| Yellow No. 6 | 2783-94-0 | yellow | 480 |
| tetracycline | 60-54-8 | yellow | N/A |
| Red No. 40 | 25956-16-6 | red | 502 |
| Red No. 3 | 16423-68-0 | red | 524 |
| Blue No. 2 | 860-22-0 | blue | 610 |
| Evan's Blue | 314-13-6 | blue | 610 |
| Green No. 3 | 2353-45-9 | green | 628 |
| Blue No. 1 | 2650-18-2 | blue | 630 |
| methylene blue | 7220-79-3 | blue | 668/609 |
| indocyanine green | 3599-32-4 | green | 800 (mostly IR) |

The dispersible chromophores listed above are generally (1) water-soluble at physiological pH, although fat-soluble chromophores (such as β-carotene) will also work if they are rapidly flushed from tissue, or (2) digestible or metabolizable through enzymatic pathways (such as methylene blue, which is rapidly metabolized by mitochondrial reductases, and proteins which are digested by proteases). In some cases, it may be possible to modify a chromophore to improve its dispersibility. A particular advantage of protein chromophores is that they can be conjugated to degradation signals using standard biochemical techniques, for example, green fluorescent protein can be conjugated to ubiquitin, which facilitates breakdown of the protein into small, invisible peptides by the eukaryotic ubiquitin proteolysis pathway.

Dispersible chromophore nanoparticles can be made from certain inert, normally indispersible colored substances which have been reduced to nanoparticles about 50 nm and smaller. Although diffuse nanoparticles might have different optical properties from the macroscopic material, when concentrated within the confined space of a microparticle core (that is, nanoparticles are closer together than the wavelength of visible light, about 500 nm), they act as a single light scatterer and/or absorber, and thus have the appearance of the original indispersible material from which they are derived. In contrast to the macroscopic material, some nanoparticles are poorly retained in tissue and are rapidly dispersed through lymphatic transport as demonstrated in lymph angiography experiments. Useful dispersible chromophore nanoparticles may be made from graphite, iron oxides, and other materials with small particle size, for example, less than 50 nm and preferably less than 5 nm.

Like the coating material, chromophore(s) 30 can be a material, or can include specific absorption component(s) 40, which strongly absorbs radiation of specific wavelength(s), particularly in the near-infrared spectral region from about 800 to 1800 nm. Absorption properties of the chromophore or specific absorption component allow the microparticle core to be selectively heated by pulses of near-infrared radiation, thus rupturing the microparticle and releasing the previously encapsulated chromophores.

Visibly colored near-infrared absorbing materials can be used as the chromophore(s) (to provide the desired detectable color) or as specific absorption component(s) in conjunction with another chromophore (to contribute to the detectable color, if desired). The infrared-absorbing visible chromophore should be rendered invisible upon exposure of the microparticles to the radiation, for example, through dispersal. Examples of useful colored near-infrared absorbing materials include, but are not limited to, graphite and amorphous forms of carbon (black), iron oxides (black or red), silicon (black), germanium (dark gray), cyanine dyes (including indocyanine green and other colors), phthalocyanine dyes (green-blue), and pyrylium dyes (multiple colors). See also U.S. Pat. No. 5,409,797 to Hosoi et al. Near-infrared absorbing materials used as specific absorption component(s) 40 can also be visibly transparent or nearly transparent at the concentrations and sizes used within the microparticles so that they do not affect the perceived color of the microparticle or of the tissue after microparticle disruption even if the material is indispersible. Useful examples include particles of filter glass (such as those manufactured by Schott, Inc.) and plastics such as polymethylmethacrylate (PMMA), as well as low concentrations of nanoparticulate graphite or other carbon. These materials can be mixed with chromophores having a desired color and then encapsulated.

Although this description has focused on near-infrared absorbing materials, materials with other properties (such as absorption of ultraviolet, visible, microwave, radio wave and other wavelengths) can also be used to construct the radiation-targeted portion of the microparticles. For example, visible materials can be incorporated into the microparticles as chromophore(s) 30, or as specific absorption component(s)

40 within the chromophore or coating material. Then visible radiation can be applied to rupture the microparticles. Useful materials include, but are not limited to, all of the visible colored dispersible chromophores listed above and other materials rendered invisible upon exposure of the microparticles to the visible radiation, for example, Oil Nile Blue N dyes, fluorescein dyes, porphyrin dyes, and coumarin dyes.

In another embodiment, chromophore(s) 30, 32, or 34 can be materials that are rendered invisible (or whose color changes) upon exposure of the microparticles to specific electromagnetic radiation without necessarily rupturing the microparticle. Bleachable chromophores (which react with a bleaching agent released by the radiation), photobleachable chromophores (altered by the radiation) or thermolabile chromophores (altered by heat produced by radiation absorption) may be used. When chromophores have undesirable toxicity, the tissue should not be exposed to them. A coating surrounding such chromophores can be made to be difficult to rupture, for example, through increased thickness or exceptional pliancy for resilience, so that exposure of the microparticles to radiation alters the color of the chromophores without rupturing the microparticles. Although dispersible materials are suitable, these chromophores need not be dispersible because they are not intended to be released.

Bleachable chromophores can be used in the microparticles depicted in FIG. 4. Most of the chromophores listed above are suitable, because they can be oxidized and rendered invisible by bleaching agents, for example, peroxides, hypochlorites (such as sodium hypochlorite, or household bleach), excited oxygen species, or free radicals. For example, a microparticle can be constructed with core chromophore FD&C Red No. 40 and sub-microparticle(s) 90 containing sodium hypochlorite as the bleaching agent 100, which is released upon exposure of the microparticle to specific electromagnetic radiation. The chromophore FD&C Red No. 40 is rendered invisible upon exposure of the microparticle to this radiation and mixing with the bleach.

Bleachable chromophores which are pH-sensitive can also be used, because they can be rendered invisible if the pH within the microparticle is changed. For example, a microparticle can be constructed with core chromophore phenolphthalein (pink to red above pH 9) in a basic alcohol solution and sub-microparticle(s) 90 containing hydrochloric acid as bleaching agent 100 which is released upon exposure of the microparticle to specific electromagnetic radiation. The chromophore phenolphthalein is rendered invisible upon exposure of the microparticle to this radiation because of reduction in pH within the microparticle.

Photobleachable chromophores that are colored until they are rendered invisible by exposure to a specific type, wavelength, and/or intensity of electromagnetic radiation include, but are not limited to, phthalocyanine (such as the zinc or chloroaluminum complexes which are green or blue); porphycenes which can be green or purple; chlorin which is a chlorophyll derivative; rhodamine dyes which can appear red, yellow, or orange and are bleached upon exposure to near-ultraviolet light; porphyrins (such as porfimer sodium, for example, PHOTOFRIN™ (Quadra Logic Technologies, Vancouver, British Columbia, Canada), a green chromophore bleached by near-ultraviolet light); Rose Bengal, bleached upon exposure to near-ultraviolet light or high intensity visible light (such as in the megawatts/$cm^2$ range); and infrared-bleached dye-paired ion compounds, cationic dye-borate anion complexes, 3-position-substituted coumarin compounds, and bis(diiminosuccinonitrilo)metal complexes, as described in U.S. Pat. No. 5,409,797 to Hosoi et al. Some chromophores are only photobleached upon simultaneous absorption of multiple photons, and are therefore unaffected by diffuse solar radiation.

A thermolabile chromophore may be any substance that becomes invisible upon heating through absorption of radiation by the chromophore or a component in contact with the chromophore which indirectly heats it. Thermolabile chromophoric mixtures can also be prepared by mixing a specific chromophore with a thermally initiated activator that releases free radicals upon heating. These free radicals then react chemically with the chromophore to render it invisible. The activators are used in the plastics industry for thermal curing of various plastics.

Microparticles 10, 50, 60, 80, or 110 constructed in accordance with any of the foregoing embodiments can also provide tissue markings that are normally invisible but can be detected under specific conditions or by specific devices. For example, materials that fluoresce, phosphoresce, wavelength up-convert, or otherwise emit visible light upon exposure to specific, often high-intensity wavelengths can be used in the microparticles. Substances can also be used which reversibly or irreversibly change color spontaneously or upon any of a variety of stimuli including changes in the chromophore's environment (such as temperature or pH) or upon exposure to energy (such as electromagnetic energy, for example, sunlight).

Methods of Making Microparticles

Using known encapsulation methods, including those described herein, it is possible to encapsulate one or more chromophores from the range described above within one or more biologically inert, substantially transparent coating materials described above to create a palette of inert, indispersible colored microparticles for implantation into tissue to create permanent markings that can be removed on demand.

The optimal method for producing a desired microparticle generally depends on the properties of the specific materials used as chromophores and coatings; this method, in turn, determines the morphology, size, and surface characteristics of the product. In the case of microparticles of the invention, the core material can be a solid particle, a concentrated liquid solution, or even a gas (in any case it can include other inert materials such as buffers, diluents, carriers, and binders), but is in most cases hydrophilic. The coating material is applied in free-flowing form, for example, liquid (solvated, monomeric, or melted) or gas/plasma, and is hardened through several processes (such as evaporation, polymerization, cooling) to form a solid shell.

Four classes of microencapsulation methods, characterized by similar technique and apparatus, are useful in the current invention. In the first class, referred to herein as "aerosol collision," aerosolized droplets or particles of core (chromophore) and coating material are made to collide, and then the coating is hardened. In the second class, referred to herein as "emulsion spraying," an emulsion of core material in coating material is atomized (into a vacuum, gas, or liquid), and then the coating is hardened. In the third class, referred to herein as "chamber deposition," coating material in a gas or plasma (very hot ionized gas) phase is deposited onto a solid core particle to form a solid shell. In the fourth class, referred to herein as "in situ encapsulation," a mixture containing the core material and coating material in the same or different emulsion phases (depending on the technique) is prepared so that coatings are formed by polymerization or seeding out around core droplets, and then the microcapsules are separated. All four classes are capable of producing microparticles within the 50 nm to 100 micron size range which are indispersible.

The coating materials and chromophores described herein are well-known and can be prepared by known methods and/or are commercially available. To prepare solid chromophore core particles of a desired size, bulk dry pigment can be ground and/or mesh-sifted or vacuum filtered (or prepared by any other suitable conventional means) as described in Standards 5 and 32 of the Metal Powder Industries Federation's *Standard Test Methods for Metal Powders and Powder Metallurgy Products,* 1993-1994 edition. Chromophore nanoparticles can also be prepared from appropriate materials in this manner. The appropriate bulk pigments can be used to prepare concentrated aqueous chromophore solutions. Materials serving as buffers, diluents, carriers, binders, etc., may be added at this stage to change the solubility, perceived color, viscosity, mobility characteristics, etc., of the chromophore preparation.

Absorption components 40 of a desired solid material and size can be prepared as described above for the chromophore, and can be mixed with melted coating materials or into liquid chromophore preparations (which can be dried, reground, and sifted to provide solid chromophore core particles incorporating additional absorption components 40).

Sub-microparticles 70 and 90 can be prepared in the same manner as microparticles and then encapsulated along with other desired core elements, usually using a method that produces significantly larger final microparticles.

If desired, a secondary or higher order coating can be added to microparticles, for example, to reduce shell permeability or to improve microparticle suspension in liquid carriers for tissue marking inks. This can be accomplished by methods in any of the microencapsulation classes defined above, particularly chamber deposition and in situ encapsulation.

A useful microencapsulation method in the aerosol collision class is described in U.S. Pat. No. 3,159,874, U.S. Pat. No. 3,208,951, and U.S. Pat. No. 3,294,204 to Langer and Yamate. In this method, opposite voltages are applied to two reservoirs containing, respectively, the heated hardenable liquid coating material and a liquid core material. The materials are atomized or aerosolized into a common chamber using high-pressure air streams that produce submicron particles of about equal size. The opposite charges of the particles cause attraction and collision, resulting in the formation of neutral coated particles which can then be cooled below the coating hardening temperature.

Appropriate materials for use in this method must be able to hold a charge, they must wet each other, and the surface tension of the core material must be higher than that of the coating material. Suitable coating materials include natural and synthetic waxes, and specifically hard waxes like carnauba wax. Core materials can be hydrophilic liquids or solids that will hold a charge (such as glycerin into which a chromophore may be mixed). The resulting mostly unagglomerated 0.5 to 1.0 micron particles are nonporous and are stable for long-term use as tissue markings.

A useful microencapsulation method in the emulsion spraying class is disclosed in U.S. Pat. No. 4,675,140 to Sparks and Mason. Solid or viscous liquid particles of core material in a prepared size range, for example, about 20 microns, can be mixed with a liquid (melted or solvated) encapsulation coating material and dispensed onto a rotating disk spinning at a speed which allows coated particles of a total size within a tight range to be flung off the apparatus into a collection chamber (for correlation between disk rotation speed and final microparticle size, see the formula in column 11, line 64, of the Sparks and Mason patent). Materials appropriate for coating lyophilized or viscous liquid hydrophilic chromophore cores include synthetic and natural waxes (such as carnauba wax) and organic polymers solvated in organic solvents. Coated particle sizes as small as about 25 microns can be achieved by this process.

Another example of a useful method in the emulsion spraying class is described in U.S. Pat. No. 5,589,194 to Tsuei. In this method, approximately one part hydrophilic, solid chromophore particles to be encapsulated are suspended in about two parts meltable coating material (such as carnauba wax) at a temperature above the coating material's melting point to form an emulsion. This step can be performed in a heated agitator (such as a turbine stirrer) and the suspension is stirred until an emulsion is formed. This emulsion is then loaded into a pressurized reactor, and a stream of the emulsion is forced into a temperature—controlled quenching agent (such as water) allowing formation and hardening of individual droplets into coated microspheres.

Other emulsion spraying methods for forming chromophore-containing microparticles include the use of rotating centrifugal force spray heads to direct emulsions of chromophores dispersed in solvated organic polymers into a cooled liquid, gas or vacuum (such as in U.S. Pat. No. 3,015,128 to Somerville).

In most emulsion spraying processes, a significant percentage of agglomerated products can be formed. When solvents are evaporated to form hardened coatings the resulting microparticles tend to be less regular and smooth, appearing wrinkled and/or collapsed compared to microparticles produced by other processes or in these processes using hardenable waxy matrices. Nevertheless, these unevenly shaped microparticles, which may contain multiple chromophore cores or pockets as shown in FIG. 5, are suitable for use in tissue markings.

A general description of a microencapsulation method in the chamber deposition class is disclosed in U.S. Pat. No. 5,718,753 to Suzuki. A substantially uniform coating of a material can be deposited onto minute solid particles of 0.05 microns and larger at thicknesses in the range of 0.01 to 0.1 microns and greater using standard vacuum deposition or sputtering techniques. Several modifications to standard vacuum deposition apparatus can be made to achieve this end, including providing for agitation of the particles in the chamber to receive a more even coating on all sides (such as by using acoustic frequency vibrations). Metal oxide materials (such as silica) are routinely deposited using such apparatus. The coating material is brought to its sublimation point by varying temperature and pressure, and the resulting gas is deposited, coating solid core particles in the chamber. To improve coating efficiency and uniformity, the dry core particles and gas can be ionized so the coating, for example, silica, is attracted to the solid, for example, a chromophore core of Rose Bengal.

Similar chamber deposition methods have been developed for coating solid particles with inert polymeric films (such as in U.S. Pat. No. 5,288,504 and No. 5,393,533 to Versic). A vacuum deposition apparatus is used to deposit a parylene (such as para-p-xylylene) or a fluorocarbon (such as TEFLON™) by pyrolysis of a monomeric, usually gas-phase material (such as di-para-xylylene in the case of xylylene deposition, or hexafluoropropylene oxide in the case of TEFLON™ deposition). Polymerization of these coating materials onto the surface of relatively cool small core particles occurs spontaneously. As in vacuum deposition or sputtering of metal oxides onto small particles, the core particles can be agitated to ensure the polymer is deposited evenly over their entire surface. The procedure can be repeated until the desired coating thickness is obtained. Coating thicknesses of under 1 micron of xylylene have been reported to give controlled release of the core substance; thicker walls offer greater protection to a chromophore core. Once polymerized, both xylylene and TEFLON™ are extremely inert materials approved for use in the body by the FDA.

Similar results can be achieved using sputtering apparatus to apply metal oxide coatings as described in U.S. Pat. No. 5,506,053 to Hubbard. In this method, a sputtering cathode is used to sputter a coating onto solid core particles of about 5 microns and larger. One feature of particles coated using chamber deposition methods is that the majority of the coatings include significant pores. The presence, number, and size of pores can be controlled by the coating thickness and by varying the conditions for coating deposition. In certain embodiments, porous microparticles are advantageous.

Useful microencapsulation methods in the in situ encapsulation class are well known in the art (see, for example, U.S. Pat. No. 5,234,711 to Kamen). The advantage of in situ encapsulation methods is that they use only standard glassware and laboratory apparatus. The coating material polymers that are useful in these in situ methods must be used with care to avoid unpolymerized species or residual reactive polymerization initiators in the resulting microparticles, either of which may have undesirable toxicological profiles. Although many organic polymer encapsulation materials have the potential to raise allergic reactions when implanted, biocompatible organic polymers approved for use in medical devices by the FDA (such as EPO-TEK™ 301 and 301-2 manufactured by Epoxy Technology) are acceptable materials that can be applied using these standard methods.

Processes that use extremely toxic organic solvents are disfavored because microparticles bearing traces of organic residues can induce local toxic reactions when implanted into tissue. This risk can be reduced by optimizing the manufacturing process and by purifying the resulting microparticles, for example, by filtration and/or washing.

In general, aqueous or hydrophilic core materials are suspended in a hydrophobic and/or organic coating solution to prevent salvation of the core phase into the coating phase. The dispersed core phase can contain materials (such as a catalyst) that induce polymerization of the coating material. For example, when an aqueous chromophore solution is dispersed in an organic phase containing cyanoacrylate monomers (which polymerize in the presence of water or base), water acts as a catalyst and cyanoacrylate coatings form around the liquid cores.

Another example in the in situ encapsulation class is disclosed in U.S. Pat. No. 5,690,857 to Osterried, wherein solid substances which are insoluble in sodium water glass solution can be coated with an outer layer of an inorganic metal salt. Using this bench-top procedure, a (hydrophilic) chromophore previously encapsulated in an organic polymer, or a hydrophobic liquid or solid chromophore, can be coated with $SiO_2$ by suspending the microparticles in water, adding sodium water glass solution, and manipulating temperature, pH, and other seeding conditions to result in a the formation of uniform coatings around the cores. Chromophore particles coated in this manner can exhibit improved suspension in aqueous vehicles for use as pigments.

Other in situ encapsulation methods can be used as long as they are capable of encapsulating the particular chromophoric core, which is in many cases hydrophilic. These other methods, many of which are described in The Kirk-Othmer Encyclopedia of Chemical Technology, 3rd ed., Vol. 16, pages 628-651, include in situ polymerization (as commonly defined and in contrast with the broader term, in situ encapsulation, used herein), simple and complex coacervation, polymer-polymer incompatibility, interfacial polymerization, and others.

When porous coatings are desired (such as to control the release of encapsulated chromophores) slight modifications can be made in the standard techniques outlined herein and/or specific materials can be used. Porous microparticles can be prepared by in situ encapsulation using certain coating materials (such as melamine formaldehyde) which have an open "netlike" structure once polymerized. In aerosol collision or emulsion spraying processes a volatile component can be added to melted coating material before capsule formation and later evaporated to leave pores, for example, in wax coatings (such as described in U.S. Pat. No. 5,589,194 to Tsuei and U.S. Pat. No. 5,204,029 to Morgan). A porous coating can be made by chamber deposition methods as described above, for example, by applying very thin coatings of a metal oxide (such as described in U.S. Pat. No. 5,376,347 to Ipponmatsu).

These and other known methods can be used to create the microparticles.

Microparticles intended for implantation in the body are preferably sterile. To ensure sterility, the manufacturing process can be carried out under sterile conditions; the finished microparticles can be exposed to gamma rays; or, if these conditions will not damage the microparticles, they can be exposed to chemicals, heat, and/or pressure (such as autoclaving) sufficient to achieve sterilization.

Methods of Use

Microparticles of the invention, regardless of how prepared, can be used as tissue marking pigments for cosmetic, identification, and other purposes. Microparticles are suspended in a liquid carrier, for example, alcohol, water, and/or glycerin, to form a tissue marking ink in the same manner as standard tattoo pigments.

The inks can be implanted into skin or similar superficial tissue with an electromagnetic coil tattooing machine (such as that disclosed in U.S. Pat. No. 4,159,659 to Nightingale); a rotary permanent cosmetics application machine (such as that disclosed in U.S. Pat. No. 5,472,449 to Chou); or with any manual tattooing device (such as the sterile single-use device marketed by Softap Inc., San Leandro, Calif.).

Alternatively, the inks can be implanted using a non-invasive method, for example, as described in U.S. Pat. No. 5,445,611 to Eppstein. This non-invasive technique is well-suited to create an even tone of pigment over a relatively large body surface area. For example, using this method a removable sun tan can be made with microparticles of the invention.

Tissue markings in skin must be properly placed to provide permanent markings. Skin is composed of the outermost epidermis, generated by the constantly dividing stratum basale, and the underlying dermis. Dermal cells, such as fibroblasts, mast cells, and others, which do not generally replicate, are located within a resilient proteinaceous matrix. It is the upper dermis, below the stratum basale, into which the microparticles are implanted to provide a tissue marking (such as a tattoo).

After implantation by any of the foregoing techniques, microparticles in the dermis form part of a permanent tissue marking if they are phagocytosed by dermal cells (most likely microparticles under about 5 microns), or if they remain in the extracellular matrix (most likely particles 5 microns and larger). Some particles will inevitably be engulfed by immune cells and relocated from the area during the healing process.

In contrast to multicolored pigment particles in standard tattoos where the body may treat different colors differently because they are different substances (one color may cause an allergic reaction or be differentially degraded over time), an advantage of the microparticles of the invention is that by implanting microparticles which bear a common coating material, diverse colors can be made to be treated by the body as though all are the same substance.

In addition to skin, microparticles of the invention can be implanted into a wide variety of living tissues comprising relatively stationary, infrequently-replicating cells. For example, the microparticles can be implanted into the internal surfaces of the body that are contiguous with the external skin, including, but not limited to, the inner surfaces of the mouth and lips, the gums and tongue, inner surfaces of the eyelid, and the tissues lining internal body passages (such as the nasal, ear, anal, urethral, and vaginal passages, and the gastrointestinal tract). Other tissues that can be marked include the tissues of and/or under the fingernails and toenails, the dentin of the teeth, and the colored iris and white sclera of the eye.

As a result of their versatility, the microparticles can be used to produce a wide variety of cosmetic tissue markings including decorative artistic tattoos that are removable and revisable; cosmetic makeup (also known as cosmetic tattooing, permanent makeup, micropigment implantation, and variations on these names) that is permanent as long as the wearer desires it; revisable corrective and reconstructive pigmentation as an adjunct to plastic surgery and to address other cosmetic problems, for example, to correct blotchy skin pigmentation (such as that due to scars or vitiligo) or to mask thinning hair by adding pigment to the scalp; and reversible addition of pigment to small or large areas of the body purely for cosmetic reasons, for example, to create the look of a tan without exposure to ultraviolet rays.

In addition to marking skin, the microparticles can be used to produce new cosmetic markings in other tissues. It is especially important that these new types of markings are removable to allow risk-free experimentation. For example, the microparticles can be implanted into areas of externally visible non-skin tissue which are important to human appearance. Colored microparticles can be added to the cornea or to the colored iris of the eye, for example, to change apparent eye color. White microparticles which are highly light-scattering can be implanted into the dentin and/or sclera, for example, to whiten the teeth and/or eyes. Colored microparticles can be added to the tissue of and/or under the fingernails and/or toenails, for example, to create solid colors, patterns, or designs for decorative purposes.

Identification markings made with the microparticles can be changed, updated, and/or removed. In some cases, selectively detectable (such as normally invisible) microparticles may be advantageous. Some examples of markings to fill identification needs include markings to assist tracking bodily sites of medical interest in external and superficial internal tissue, for example, marking a radiation therapy field on the skin, or marking a colon polyp in the intestine which can subsequently be monitored endoscopically; identification markings for humans, for example, emergency information regarding an individual's medical history, "dog-tags" on military personnel, and identification markings on newborn babies to ensure no hospital mix-ups; and identification markings for animals (such as wild animals, livestock, sport/show animals, and pets), for example, information markings for the return of lost pets.

Removal Methods

Tissue markings of the invention can be removed by applying specific energy (such as electromagnetic radiation), preferably that energy by which the microparticles used to create the tissue marking were designed in advance to be removed. Some microparticles are designed to be ruptured, releasing into the bodily fluids the dispersible chromophores which are then metabolized or relocated from the tissue marking site. Other microparticles are designed to remain intact while the chromophoric properties of the encapsulated chromophores within the microparticle are altered, rendering the microparticles invisible.

For removal of all tissue markings created using microparticles of the invention described in detail herein, the marking site is exposed to a specific type of electromagnetic energy (such as coherent or incoherent light by which the microparticles comprising the marking were designed in advance to be removed). The energy is applied using an external source (such as a laser or flash-lamp at specific wavelengths) at a specific intensity and for a controlled length of time. The exposure can be administered in one or several pulses. A range of electromagnetic radiation, for example, ultraviolet, visible, infrared, microwave, and radio wave, may be suitable for removing the tissue markings. The preferred wavelengths are those which the microparticles were specifically designed in advance to absorb, for example, by use of specific radiation absorbing materials within the microparticle.

The microparticles are designed in advance to be removed using devices emitting safe forms of energy which are minimally absorbed by ubiquitous energy absorbing substances normally present in the body. These substances include water which absorbs at 1800 nm and greater; melanin which absorbs at up to about 1100 nm, but absorbs far less energy at wavelengths over 800 nm; and oxyhemoglobin which has a maximal absorbance in the range of 400 to 600 nm. Thus, a desirable spectral region is the near-infrared, specifically about 800 to 1800 nm. As noted earlier, many useful materials are available which absorb in this near-infrared range. Certain types of microwaves and radio waves can also be very specific and safe.

In theory, external devices producing safe energy other than electromagnetic radiation can be used to remove tissue markings which are specifically designed in advance for removal by this energy. For example, intense ultrasound waves are capable of causing cavitation, or the rapid expansion and collapse of gas bubbles, within the tissue. The threshold for initiating cavitation depends on the local intensity and frequency of ultrasound waves, and on the material's acoustic, mechanical, and thermal properties. Cavitation is initiated more easily when ultrasound waves interact with an existing gas bubble, causing the absorption and scattering of waves. Stable gas microbubbles have recently been employed, for example, as contrast agents for medical ultrasound imaging. It is theoretically possible to construct chromophoric microparticles that contain stable encapsulated gas bubbles designed in advance to enhance ultrasound-induced cavitation and rupture of the microparticles. Electromagnetic radiation, however, can supply more energy specifically to the microparticles; it is the preferred energy for removal and is therefore described in greater detail herein.

The method of removing standard tattoos by irradiation with a laser takes advantage of the physical phenomenon of selective radiation absorption by colored substances. For instance, the ruby laser which emits coherent red light of 694 nm is most strongly absorbed by green, black, and blue chromophores (such as tattoo pigments in the skin). Accordingly, the ruby laser is now used to treat standard green, black, and blue tattoos. Methods of removing tissue markings of the invention similarly exploit the selective absorption of electromagnetic radiation by various components of the microparticles, but in a very different way.

In contrast to standard tattoos, microparticles of the invention can be designed in advance such that multiple colored microparticles (such as red, green, and white, which are optimally treated with separate lasers in standard tattoos) all selectively absorb radiation of the same wavelength regardless of their apparent color. This feature is accomplished by using common radiation-absorbing material(s) in all colors (such as coating 20 or specific absorption component(s) 40) which enables removal of diverse microparticles using a common energy type(s). For example, a multicolored tattoo of the invention can be designed such that all colors are removed in a treatment with a Nd:YAG laser emitting 1064 nm pulses which target a common carbon absorption component 40 in all tissue marking microparticles.

Dispersible chromophore-containing microparticles (such as those constructed according to FIGS. 1, 2, 3, and 5) are designed in advance to be removed using electromagnetic radiation which ruptures the microparticles, thereby releasing the chromophores. Radiation absorption by an absorbing coating 20, chromophore(s) 30 or 32, or an additional absorption component(s) 40 located in the coating or the chromophore core (depending on the microparticle's design) causes the coating to rupture. Cells in the tissue may or may not be ruptured concomitantly, depending on the amount of energy applied and the pulse length in which it is delivered; after irradiation, chromophore dispersal occurs through physiological processes in both cases and the marking is removed from the tissue. The total systemic dose of the released chromophores (stains, dyes, drugs, or proteins) is generally low following a removal treatment.

The amount of energy per unit area (fluence) required to rupture microparticles 10, 50, 60, and 100 made with given target materials (such as a specific absorption component 40 or an absorbing coating 20) can be determined. The fluence (E) can be estimated based on the optical absorption coefficient ($\mu a$) and the heat capacity ($\rho c$), which are known for different materials, and the required change in temperature to cause breakage ($\Delta T$), from the following equation:

$$E = \Delta T \rho c / \mu a.$$

The temperature change ($\Delta T$) can be set, for example, at 100° C. to provide for vaporization/rapid expansion of an aqueous core, ensuring destruction of microparticles; other values can be chosen for other types of core materials. Mechanical stress induced by rapid heating and/or differential expansion of the coating can provide additional mechanisms for microparticle rupture. Heating of the coating, the chromophore, absorption component 40, or any combination can be responsible for microparticle rupture and therefore the value of $\Delta T$ required for rupture of differently constructed microparticles may vary considerably. For example, for microparticles made with a coating of Schott filter glass KG-3, a fluence of about 20 Joules/cm$^2$ is sufficient to achieve a 100° C. temperature change based upon the above equation using the known optical absorption coefficient for KG-3 of about 20 cm$^{-1}$ at a wavelength of 1064 nm (such as from a Nd:YAG laser) and its heat capacity of about 4 Joules/cm$^3$/° C.

In general, visible and near-infrared fluences of about 0.1 to 30 Joules/cm$^2$ are applied, and are well tolerated by the skin. 1.0 to 5.0 Joules/cm$^2$ are most suitable, but higher laser fluences that do not injure the tissue can be used, and lower fluences can be used as long as they rupture the microparticles.

The preferred electromagnetic radiation pulse duration used to effect mechanical rupture or thermal alteration of a microparticle is approximately less than or equal to the thermal relaxation time of ($\tau_r$) of the microparticle (see Anderson, R. R. and J. A. Parrish (1983). *Science* 220: 524-527). To a close approximation, $\tau_r$ in seconds is equal to d$^2$, where "d" is the target diameter in millimeters. This pulse duration results in thermal confinement at the microparticle, reducing secondary damage to surrounding tissue. For example, a 100 nm (10$^{-4}$ mm) diameter particle (such as a 100 nm absorption component 40 in a 10 micron diameter microparticle) is preferably treated with a pulse duration of less than or equal to about (10$^{-4}$)$^2$ or 10$^{-3}$ seconds (10 nanoseconds). In general, the energy can be delivered in pulses ranging from 0.1 to about 100, 500, or 1000 nanoseconds. Typical Q-switched lasers operate in this range. Within this range, pulses of 0.5 to 100 nanoseconds are preferred.

Current radiation systems useful to remove tissue markings according to the first removal method include Q-switched near-infrared lasers presently used in standard tattoo removal treatments (such as the 1064 nm Q-switched Nd:YAG or 760 nm Alexandrite lasers), as well as intense pulsed light sources where the wavelength range can be varied into the near-infrared (such as the Photoderm VL/PL marketed by ESC Medical Systems, Yokneam, Israel).

In general, the total amount of radiation necessary to remove tissue markings of the invention can be reduced compared to standard laser therapy to remove standard tattoos because the electromagnetic absorption and/or structural properties of the microparticles are carefully chosen in advance with removal in mind. This reduction means less secondary damage is incurred by surrounding cells, and patient pain is reduced.

In removing tissue markings made using microparticles which are rendered invisible without being ruptured, as described hereafter, the tissue can experience even less trauma than in the embodiments described above. Cells are unlikely to be damaged during tissue marking removal or even to be "aware" of treatment.

Bleachable chromophore-containing microparticles (such as those constructed according to FIG. 4) are designed in advance to be removed using electromagnetic radiation which ruptures sub-microparticle(s) 90 containing bleaching agent(s) 100 without rupturing the entire microparticle 80. This method can be practiced by following the guidelines above to determine how much of a given type of energy should be applied to rupture the sub-microparticle through absorption by coating 95, specific absorption component 40, and/or bleaching agent 100. The electromagnetic radiation should be administered using a device emitting wavelengths which are not strongly absorbed by the coating 20 or chromophore(s) 34. A conservative dose should always be administered in this case to avoid rupturing the entire microparticle which could cause leakage of reactive compounds into the tissue. Once the bleaching agent mixes with the chromophore, the tissue marking will become invisible at completion of (1) the oxidation reaction, or (2) the pH transition.

Photobleachable chromophore-containing microparticles (such as those constructed according to FIG. 1, 2, 3, or 5) are designed in advance to be removed using electromagnetic radiation which affects the specific chromophore(s) 30 or 32 without rupturing the entire microparticle 10, 50, 60, or 110. Once exposed to that radiation in an appropriate dosage, the chromophore loses its visible color because of an irreversible chemical transition or decomposition, and the tissue marking is removed. Again, the radiation administered should not be strongly absorbed by coating 20. For example, to remove the photobleachable chromophores PHOTOFRIN™ and Rose Bengal, specific ultraviolet light or high intensity visible light pulses (such as from an excimer laser, optical-parametric oscillator, or Nd:YAG laser harmonic frequencies) are administered.

Thermolabile chromophore-containing microparticles (such as those constructed according to FIG. 1, 2, 3, or 5) are designed in advance to be removed using electromagnetic radiation tuned to heat the chromophore core(s) without rupturing the entire microparticle 10, 50, 60, or 110. For example, radiation may be absorbed by and heat the chromophore to or above a specific temperature at which its chromophoric properties are changed or lost either by an irreversible chemical transition or tertiary structure disruption. Thermal destruction can be facilitated by free radicals released from a thermally initiated activator mixed into the chromophore core(s) which render the microparticle invisible upon heating.

Some patients may desire partial removal of a tissue marking which is also achieved by irradiation. Incomplete removal can be achieved, for example, by administering lower doses of radiation to affect only a fraction of microparticles, or by only treating certain areas of the tissue marking. It may be desirable, for example, to reduce the size of the marking (such as to thin a cosmetic eyebrow or eyeliner); to remove a portion of a marking including a smaller mark, symbol, text, or identifying information (such as to remove a name from a vow tattoo); to reduce the color-intensity of a marking (such as to lighten a dark lipliner); or to transform the appearance of the tissue marking (such as to create a decorative light-on-dark pattern within a previously solid dark tissue marking).

In the event that a new tissue marking is desired to replace an existing marking, radiation is used to remove all or part of the original marking. Colored microparticles are then implanted into the tissue. The process could be used to update marks (such as bar codes), symbols, text, or identifying information, for example, to change a phone number marking on a pet after a move; to rework or refresh the appearance of the remaining tissue marking, for example, to add details to an artistic tattoo after regions have been removed to reduce the tattoo size; or to replace completely the original marking with a new tissue marking.

EXAMPLES

The following examples illustrate but do not limit the scope of the invention, which is defined by the claims.

Example 1

Preparation of Blue Microparticles Ruptured by Infrared Radiation

Microparticles that are blue in color, and that are preferentially heated, and thus ruptured, by infrared radiation, are prepared by first suspending crystalline methylene blue in glycerin to obtain a liquid blue chromophore.

The coating material is prepared by heating carnauba wax to about 95° C. (above its melting point of about 85° C.) and mixing into the molten wax 3 percent graphite nanoparticles (about 20 to 100 nm) until a uniform mixture is obtained. The liquid coating material is given a net positive charge, while the liquid chromophore is given a negative charge, for example, in a device as described in Langer et al., *J. Colloid interface Sci.*, 29:450-455 (1969). The two charged liquids are atomized and sprayed into a chamber to collide and form coated microparticles, which are hardened as they drop through cold air in the chamber. The resulting 0.5 to 1.0 micron microparticles are washed in distilled, deionized water, and are then separated and dried. They can then be sterilized by gamma radiation.

The blue microparticles can be suspended in a sterile solution of 50% glycerin, 25% water, and 25% isopropyl alcohol to form a tattoo ink, and can be implanted using standard tattoo needles to provide a permanent blue tissue marking.

The marking can be removed at any time by irradiating the marking with near-infrared light from a Q-switched Nd:YAG laser (at a wavelength of 1064 nm) for 10 nanoseconds at a fluence of 12 Joules/cm$^2$, which causes the graphite to heat and rupture the coating of the microcapsules, allowing the methylene blue to disperse and be digested by the cells in the tissue. Alternatively, an optical-parametric oscillator can be used to produce 670 nm, 10 nanosecond pulses which are strongly absorbed by methylene blue, heating and rupturing the microparticles.

Example 2

Preparation of Yellow Microparticles Ruptured by Infrared Radiation

Microparticles that are yellow in color, and that are preferentially heated, and thus ruptured, by infrared radiation, are prepared by grinding and sifting dry, powdered tetracycline to obtain uniform particles of about 30 microns, with a 95% size range of 20 to 40 microns, using U.S. Standard Mesh No. 325. These dry tetracycline particles form chromophore cores.

The coating material is prepared by heating carnauba wax to about 95° C. and mixing into the molten wax 3 percent graphite nanoparticles (about 20 to 50 nm) until a uniform mixture is obtained. The dry tetracycline particles are dispersed in the molten wax/graphite mixture, and a stream of the liquid mixture is dispensed onto an 8 inch diameter heated disk spinning at a rate of 11,100 rpm (such as described in U.S. Pat. No. 4,675,140 to Sparks et al.). The disk spins off wax droplets containing chromophore cores. These droplets harden into microparticles and are collected in a chamber. The resulting microparticles have an average size of about 40 microns and contain about 56% (by weight) chromophore core material. The microparticles are washed in distilled, deionized water, and are then separated and dried. The wash water can be analyzed in a spectrophotometer to test for leakage of tetracycline from the final microparticles. The microparticles can be sterilized using gamma radiation.

The yellow microparticles can be suspended in a sterile solution of 50% glycerin, 25% water, and 25% isopropyl alcohol to form a tattoo ink, and can be implanted using standard tattoo needles to provide a permanent yellow tissue marking.

The marking can be removed at any time by irradiating the marking with near-infrared light from a Q-switched Nd:YAG laser at a wavelength of 1064 nm for 10 nanoseconds at a fluence of 12 Joules/cm$^2$, which causes the graphite to heat and rupture the coating of the microcapsules, allowing the tetracycline to be dispersed from the site of implantation in the tissue.

Example 3

Preparation of Red Microparticles that Contain Chromophores Rendered Invisible by Ultraviolet Radiation Microparticles that are red in color, and that are photobleached and rendered invisible by ultraviolet radiation, are prepared by grinding dry powdered Rose Bengal and sifting it to obtain uniform particles of about 30 microns using U.S. Standard Mesh No. 325 to create solid chromophore cores.

Microparticles of solid Rose Bengal encapsulated in a parylene film are prepared with the core material being placed in the deposition reaction chamber as generally described in U.S. Pat. No. 5,393,533 to Versic. Parylene C dimer is heated in the pyrolysis boat to 690° C. and is vaporized and deposited at a vapor temperature of 171° C. onto the agitated core material over a period of 3 hours. The procedure is repeated to increase the thickness of the parylene coating. After 5 iterations, a coating thickness of 1 micron is achieved.

The microparticles are coated again with $SiO_2$ to ensure that they will not rupture once implanted in a tissue. First, as generally described in U.S. Pat. No. 5,690,857 to Osterried et al., the initial microparticles are suspended in deionized water in a concentration from 3 to 10% by weight, and heated to a temperature of 60° C. while stirring. The pH is adjusted to 9.0 by addition of NaOH. A sodium water glass solution (1:1 dilution with water) is slowly added, and the pH of the resulting mixture is maintained at 9.0 by simultaneous addition of HCl. The mixture is stirred for 15 minutes, the pH is lowered to 6.5, and the mixture is stirred for another 15 minutes. Anhydrous $Na_2SO_4$ and $AlCl_3.6H_2O$ are added, and the temperature of the mixture is raised to 95° C. for 30 minutes. The mixture is cooled, and the liquid is removed from the recoated microparticles. The resulting recoated microparticles of about 40 to 45 microns in diameter are washed in distilled, deionized water, and are then separated and dried. They can be sterilized by gamma radiation.

The red microparticles can be suspended in a sterile solution of 50% glycerin, 25% water, and 25% isopropyl alcohol to form a tattoo ink, and can be implanted using standard tattoo needles to provide a permanent blue tissue marking.

The tissue marking can be removed at any time by irradiating the site with near-ultraviolet light from an excimer laser at a wavelength of 351 nm for 10 nanoseconds at a fluence of up to about 5 Joules/cm$^2$, which causes the Rose Bengal to photobleach, rendering the microparticles invisible. The extent of photobleaching can be controlled by adjusting fluence per pulse and number of pulses administered.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A tissue marking ink comprising:
   a particle comprising a thermolabile chromophore that becomes invisible upon heating by application of a specific energy; and
   a carrier.

2. The ink of claim 1, wherein the particle further comprises a component in contact with the chromophore that indirectly heats the chromophore upon application of the specific energy.

3. The ink of claim 1, wherein the particle further comprises a thermally initiated activator mixed into the chromophore that releases free radicals upon heating by application of the specific energy.

4. The ink of claim 1, wherein the specific energy is electromagnetic radiation.

5. The ink of claim 1, wherein the specific energy is infrared or near-infrared radiation.

6. The ink of claim 1, wherein the appearance of the chromophore changes when the specific energy is applied once.

7. The ink of claim 1, wherein the chromophore has an average particle size of less than about 50 nm.

8. The ink of claim 1, wherein the chromophore changes from an initial color to a different color upon exposure of the particle to the specific energy.

9. The ink of claim 1, wherein the particle further comprises:
   an indispersible, biologically inert coating; and
   a core enveloped within the coating, wherein the core comprises the chromophore.

10. The ink of claim 9, wherein the coating comprises a metal oxide, silica, glass, fluorocarbon resin, organic polymer, wax, or a combination thereof.

11. The ink of claim 9, wherein the coating is substantially visibly transparent and absorbs near-infrared radiation.

12. The ink of claim 9, wherein multiple cores are enveloped within the coating of a single particle.

13. The ink of claim 9, wherein the chromophore is detectable through the coating.

14. The ink of claim 9, wherein the coating comprises from about 10 to about 95 percent of the volume of the particle.

15. The ink of claim 1, wherein the particle is from about 50 nm to about 100 microns in size.

16. The ink of claim 1, wherein the particle is from about 15 nm to about 500 nm in size.

17. The ink of claim 1, wherein the particle is less than about 50 nm in size.

18. The ink of claim 1, wherein the particle is less than about 5 nm in size.

19. The ink of claim 1, wherein the carrier comprises at least one of alcohol, water, or glycerin.

20. A method of applying a tissue marking, the method comprising:
   providing the tissue marking ink of claim 1; and
   implanting said ink into a tissue to form a tissue marking, wherein the chromophore becomes invisible upon exposure to a specific energy when the ink is within the tissue.

21. The method of claim 20, wherein the specific energy is electromagnetic radiation.

22. The method of claim 20, wherein the specific energy is infrared or near-infrared radiation.

23. A method for altering a tissue marking implanted in tissue, wherein the tissue marking comprises the ink of claim 1, wherein the chromophore that becomes invisible upon heating by application of a specific energy when the ink is within the tissue, the method comprising exposing the tissue marking to the specific energy for a sufficient time to render the chromophore substantially invisible.

24. The method of claim 23, wherein the specific energy is electromagnetic radiation.

25. The method of claim 23, wherein the specific energy is infrared or near-infrared radiation.

26. A tissue marking ink comprising a particle, wherein the particle comprises polymethylmethacrylate (PMMA) and an iron oxide absorption component, wherein the particle ruptures upon exposure to a specific energy when the particle is within a tissue.

27. The tissue marking ink of claim 26, further comprising a chromophore.

28. The tissue marking ink of claim 27, wherein the chromophore is a Food and Drug Administration (FDA)-approved dye.

29. The tissue marking ink of claim 27, wherein the chromophore is selected from the group consisting of phthalocyanine dyes, cyanine dyes, and pyrylium dyes.

30. The tissue marking ink of claim 27, wherein the chromophore is carbon black.

31. The tissue marking ink of claim 27, wherein the chromophore is selected from the group consisting of rifampin, β-carotene, tetracycline, indocyanine green, Evan's blue, and methylene blue.

32. The tissue marking ink of claim 27, wherein the chromophore is selected from the group consisting of FD&C Blue No. 2, FD&C Blue No. 1 (Brilliant Blue FCF), FD&C Green No. 3 (Fast Green FCF), FD&C Red No. 3 (Erythrosine), FD&C Red No. 40 (ALLURA™ Red AC), FD&C Yellow No. 5 (Tartrazine), and FD&C Yellow No. 6 (Sunset Yellow FCF).

33. The tissue marking ink of claim 27, wherein the chromophore is a soluble inorganic salt selected from the group consisting of copper sulfate, $Cu(NH_3)^{2+}$, $MnO_4$, $NiCl_2$, $CrO_4$, and $Cr_2O_7^{2-}$.

34. The tissue marking ink of claim 27, wherein the chromophore is white.

35. The tissue marking ink of claim 27, wherein the chromophore is yellow.

36. The tissue marking ink of claim 27, wherein the chromophore is blue.

37. The tissue marking ink of claim 27, wherein the chromophore is green.

38. The tissue marking ink of claim 27, wherein the chromophore is red.

39. The tissue marking ink of claim 26, wherein the particle is less than about 5 microns in diameter.

40. The tissue marking ink of claim 26, wherein the particle is in the nanometer size range.

41. The tissue marking ink of claim 26, wherein the particle is suspended in a liquid carrier.

42. The tissue marking ink of claim 41, wherein the carrier comprises alcohol, water, or glycerin, or any combination thereof.

43. The tissue marking ink of claim 26, wherein the specific energy is laser radiation.

44. A method of applying a tissue marking, the method comprising:
providing the tissue marking ink of claim 26; and
implanting the particle into a tissue to form a tissue marking.

45. A method for rendering undetectable a tissue marking implanted in tissue, the tissue marking comprising a particle comprising polymethylmethacrylate (PMMA), an iron oxide absorption component, and a chromophore, wherein the particle is rendered undetectable upon exposure to a specific energy when the particle is within a tissue, the method comprising exposing the tissue marking to the specific energy for a sufficient time to render the particle undetectable.

46. The method of claim 45, wherein the specific energy is laser radiation.

* * * * *